United States Patent [19]

Ono et al.

[11] Patent Number: 5,696,804
[45] Date of Patent: Dec. 9, 1997

[54] X-RAY TOMOGRAPHIC APPARATUS

[75] Inventors: Katsuhiro Ono, Utsunomiya; Koichi Kitade; Hidero Anno, both of Otawara; Takayuki Kitami, Tochigi, all of Japan

[73] Assignee: Kabushiki Kaisha Toshiba, Kawasaki, Japan

[21] Appl. No.: 790,792

[22] Filed: Jan. 30, 1997

[30] Foreign Application Priority Data

Jan. 31, 1996 [JP] Japan ................... 8-015641
Dec. 25, 1996 [JP] Japan ................... 8-344736

[51] Int. Cl.⁶ .............................................. H01J 35/10
[52] U.S. Cl. .............................. 378/4; 378/125; 378/131
[58] Field of Search ........................... 378/4, 125, 126, 378/131, 132, 133, 139, 144, 15, 146

[56] References Cited

U.S. PATENT DOCUMENTS

| | | | |
|---|---|---|---|
| 4,210,371 | 7/1980 | Gerkema et al. | 378/125 |
| 4,562,587 | 12/1985 | Gerkema et al. | 378/125 |
| 4,641,332 | 2/1987 | Gerkema | 378/125 |
| 4,644,577 | 2/1987 | Gerkema et al. | 378/133 |
| 4,819,259 | 4/1989 | Tanaka | 378/125 |
| 4,856,039 | 8/1989 | Roelandse et al. | 378/133 |
| 5,068,885 | 11/1991 | Vetter | 378/133 |
| 5,077,775 | 12/1991 | Vetter | 378/132 |
| 5,140,246 | 8/1992 | Rarick | 318/779 |
| 5,212,437 | 5/1993 | Hescht et al. | 318/798 |
| 5,228,070 | 7/1993 | Mattson | 378/4 |
| 5,448,610 | 9/1995 | Yamamoto et al. | 378/19 |

FOREIGN PATENT DOCUMENTS

| | | |
|---|---|---|
| 0 141 475 | 5/1985 | European Pat. Off. . |
| 0 467 532 | 1/1992 | European Pat. Off. . |
| 0 569 238 | 11/1993 | European Pat. Off. . |
| 58-023199 | 2/1983 | Japan . |
| 62-069495 | 3/1987 | Japan . |
| 6-196113 | 7/1994 | Japan . |

*Primary Examiner*—Don Wong
*Attorney, Agent, or Firm*—Cushman Darby & Cushman IP Group of Pillsbury Madison & Sutro LLP

[57] ABSTRACT

In an X-ray tomographic apparatus, while rotating a gantry rotary section around a region where an object to be photographed is placed, the anode target of an X-ray tube is rotated at a predetermined high rotation rate and X-rays are emitted from the anode target. In emitting the X-rays, the rotation torque is increased to be larger than that prior to rotation of the gantry rotary section in accordance with the rotation drive power supplied to a stator coil. A decrease in rotation rate of the anode target of the X-ray tube can be prevented even during rotation of the gantry rotary section, radiation at a necessary and sufficient X-ray dose can be assured, and an X-ray tomographic image can be properly obtained.

13 Claims, 6 Drawing Sheets

X-RAY TOMOGRAPHIC APPARATUS

BACKGROUND OF THE INVENTION

The present invention relates to an X-ray tomographic apparatus and, more particularly, to an X-ray tomographic apparatus having an x-ray tube incorporating a hydrodynamic bearing using a liquid metal lubricant as a lubricant.

For example, an X-ray tomographic apparatus known as a CT scanner is very popular in the fields of medical and industrial applications. In a tomographic apparatus requiring a large X-ray dose, particularly, an X-ray tube of a rotary anode type is frequently used as an X-ray radiation source. This X-ray tube is fixed together with an X-ray detector in a gantry rotary section in a predetermined positional relationship.

In the X-ray tube of a rotary anode type, as is known well, a disk-like anode target is fixed to a rotary structure, and the rotary structure is mechanically supported through a bearing section by a stationary structure having this bearing section. An electromagnetic coil of a stator is disposed outside a vacuum vessel in correspondence with the rotary structure. A rotation drive power is supplied to this electromagnetic coil to rotate the anode target at a high rotation rate, e.g., 150 rps. An electron beam emitted from a cathode impinges on the rotating anode target, and X-rays are radiated from the anode target.

A CT scanner for performing X-ray photography by rotating the anode target at a high rotation rate is disclosed in Jpn. Pat. Appln. KOKAI Publication No. 58-23199, 62-69495, or 6-196113, or U.S. Pat. No. 5,140,246.

The bearing section of the X-ray tube which rotatably supports the rotary structure is constituted by a rolling bearing such as a ball bearing, or a hydrodynamic sliding bearing which has a helical groove formed in the bearing surface and uses a liquid metal lubricant such as gallium (Ga) or a gallium-indium-tin (Ga-In-Sn) alloy which is kept in the liquid state at least during the operation.

In an X-ray CT scanner equipped with an X-ray tube of a rotary anode type having the former ball bearing, the rotation resistance of the ball bearing is relatively low, so that the rotation rate of the anode target is reduced little even during rotation of the gantry rotary section. In an X-ray tube of this rotary anode type, the rotation rate of the rotary structure can be increased to 150 rps or more. X-ray exposure can be continued for a predetermined period of time to perform tomography while maintaining this rotation rate of the rotary structure.

In the CT scanner equipped with the X-ray tube using the ball bearing, however, in order to prevent the service life from becoming short due to scattering and consumption of a lubricant consisting of a solid soft metal in the bearing, the rotary structure and the anode target are kept stopped before and after X-ray photography, i.e., X-ray exposure, and the rotation rates of the rotary structure and the anode target are increased within a short period of time immediately before X-ray photography. There is also an apparatus in which a rotary structure and an anode target are controlled to be electrically braked to stop their rotation as soon as possible at the end of X-ray exposure.

An example using the latter hydrodynamic slidebearing is disclosed in U.S. Pat. No. 4,210,371 issued Jul. 1, 1980, J. Gerkema corresponding to Jpn. Pat. Appln. KOUKOKU Publication No. 60-21463. There are also disclosed in U.S. Pat. No. 4,562,587 issued Dec. 31, 1985, J. Gerkema et. al corresponding to Jpn. Pat. Appln. KOKAI Publication No. 60-97536, U.S. Pat. No. 4,641,332 issued Feb. 3, 1987, J. Gerkema corresponding to Jpn. Pat. Appln. KOKAI Publication No. 60-117531, U.S. Pat. No. 4,644,577 issued Feb. 17, 1987, J. Gerkema et. al corresponding to Jpn. Pat. Appln. KOKAI Publication No. 60-160552, U.S. Pat. No. 4,856,039 issued Aug. 8, 1989, C. D. Roelandse corresponding to Jpn. Pat. Appln. KOKAI Publication No. 62-287555, U.S. Pat. No. 5,068,885 issued Nov. 26, 1991, A. Vetter corresponding to Jpn. Pat. Appln. KOKAI Publication No. 2-227947, and U.S. Pat. No. 5,077,775 issued Dec. 31, 1991, A. Vetter corresponding to Jpn. Pat. Appln. KOKAI Publication No. 2-227948.

In the hydrodynamic bearing of the X-ray tube of this rotary anode type, as described in the above prior-art publication, the bearing surface of a rotary or stationary structure has a helical groove like a herringbone pattern having a depth of, e.g., 20 μm. A predetermined dynamic pressure is generated in the bearing section in a high-rate rotation of the rotary structure at a predetermined rotation rate. The bearing surfaces of the rotary and stationary structures maintain a bearing gap of about 20 μm, so that the rotary structure is rotated in a substantially non-contact manner. For this reason, the shape and size of the helical groove constituting the bearing, and the bearing gap during the operation are designed to generate an optimal dynamic pressure in consideration of the installation state of the X-ray tube in use, the weight of the rotary structure, and the like.

The X-ray tube of the rotary anode type having the hydrodynamic bearing has a higher rotation resistance in the bearing section than that in the ball bearing. A very large rotation drive power is required to perform high-rate rotation at 150 rps or more. In the X-ray CT scanner equipped with the X-ray tube of the rotary anode type having this hydrodynamic bearing, when a gantry rotary section is rotated for tomography, the rotation rate of the anode target of the X-ray tube is considerably reduced.

For example, even if the rotation rate of the anode target of the X-ray tube is set to 50 rps (revolutions per second) enough to perform X-ray radiation while the gantry rotary section is kept stopped, the rotation rate of the anode target drops to, e.g., about 40 rps during rotation of the gantry rotary section. Accordingly, some implementation is required to reduce the amount of electron beam incident on the target so as to prevent damage to the anode target.

The rotation rate of the anode target of the X-ray tube falls during rotation of the gantry rotary section due to the following reason. The centrifugal force acting on the X-ray tube upon rotation of the gantry rotary section is large. For this reason, the resistance (e.g., loss) generated in the bearing section of the X-ray tube upon rotation becomes high. Although an increase in rotation resistance upon rotation of the gantry rotary section does not pose any serious problem in a ball bearing, the rotation resistance generated by the above centrifugal force is non-negligibly high in the hydrodynamic sliding bearing. In addition, demand has recently arisen for obtaining tomographic images for a larger number of portions of an object to be photographed within a short period of time. The centrifugal force acting on the anode target of an X-ray tube tends to increase because the weight of the anode target of the X-ray tube must be increased to increase the X-ray dose radiated from the X-ray tube, the rotation rate of the gantry rotary section must be increased, or a high-rotation rate helical scan mode must be employed. In particular, recently, the rotation rate of the gantry rotary section tends to increase to one revolution per second (rps) or more in X-ray photography in the high-rate rotation helical scan mode. In this case, a considerably large centrifugal force acts on the X-ray tube. The higher the rotation rate of the gantry rotary section, the higher the rotation resistance of the hydrodynamic bearing section of the X-ray tube. The rates of reductions in rotation rates of the rotary structure and the anode target become high.

BRIEF SUMMARY OF THE INVENTION

It is an object of the present invention to provide an X-ray tomographic apparatus capable of performing radiation at a sufficient X-ray dose to obtain X-ray tomographic images so as not to reduce the rotation rate of the anode target of the X-ray tube even during rotation of a gantry rotary section.

According to the present invention, there is provided an X-ray tomographic apparatus comprising rotation torque control means for switching a rotation torque of a rotary structure of an X-ray tube, which is obtained during rotation of a gantry rotary section, to an average rotation torque larger than an average continuous rotation torque prior to rotation of the gantry rotary section.

Additional object and advantages of the invention will be set forth in the description which follows, and in part will be obvious from the description, or may be learned by practice of the invention. The object and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Figure 1:
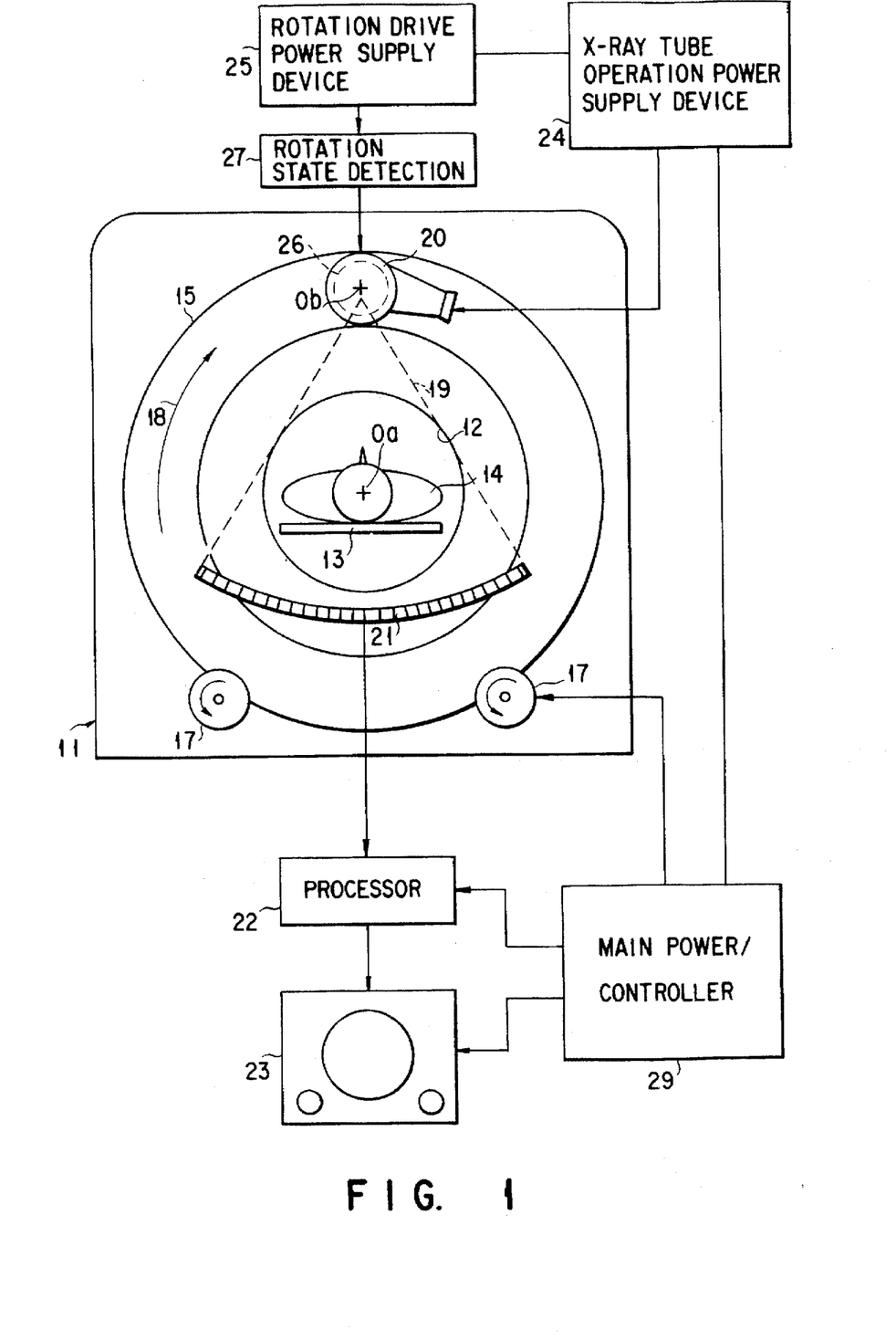
FIG. 1 is a block diagram schematically showing an X-ray tomographic apparatus according to an embodiment of the present invention.

An X-ray tomographic apparatus according to an embodiment of the present invention will be described with reference to the accompanying drawing. Throughout the drawing, the same reference numerals denote the same parts. An X-ray CT scanner whose schematic arrangement is shown in FIG. 1 has a structure in which a reciprocally movable bed or coach 13 and an object to be photographed, i.e., an ROI (Region Of Interest) 14 placed on the bed 13 are disposed inside a dome 12 formed at the central portion of a gantry 11. A gantry rotary section 15 constituted by a ring-like frame is disposed inside the gantry 11. During photography, the gantry rotary section 15 is rotated around the ROI 14 by rotation drive devices 17 that operate under the control of a main power/controller 16, as indicated by an arrow 18.

An X-ray tube device 20 for radiating a fan beam of X-rays 19 as indicated by the dotted lines in a direction toward the ROI 14 is attached to the gantry rotary section 15 at a predetermined position. An X-ray detector 21 is arranged at a side opposite to the X-ray tube device 20 with respect to the ROI 14. During X-ray photography, i.e., in the photographic mode, the X-ray detector 21 and the X-ray tube device 20 are rotated around the ROI 14 while maintaining the positional relationship between them. An X-ray image signal obtained from the X-ray detector 21 is supplied to and processed by a computer image signal processor 22. An image output signal from the processor 22 is supplied to a CRT monitor 23, thereby displaying the tomographic image of the ROI 14.

The X-ray tube device 20 receives a rotation drive power from an X-ray tube operation power supply device 24 and a rotation drive power supply device 25 to rotate the rotary structure and an anode target 26 in the X-ray tube. A rotation state detector 27 for detecting the rotation drive power or the rotation state of the rotary structure is connected to the rotation drive power supply device 25. Note that in this embodiment, a central axis Oa of rotation of the gantry rotary section 15 is parallel or almost parallel to a rotation axis Ob of the anode target 26 of the X-ray tube.

Figure 2:
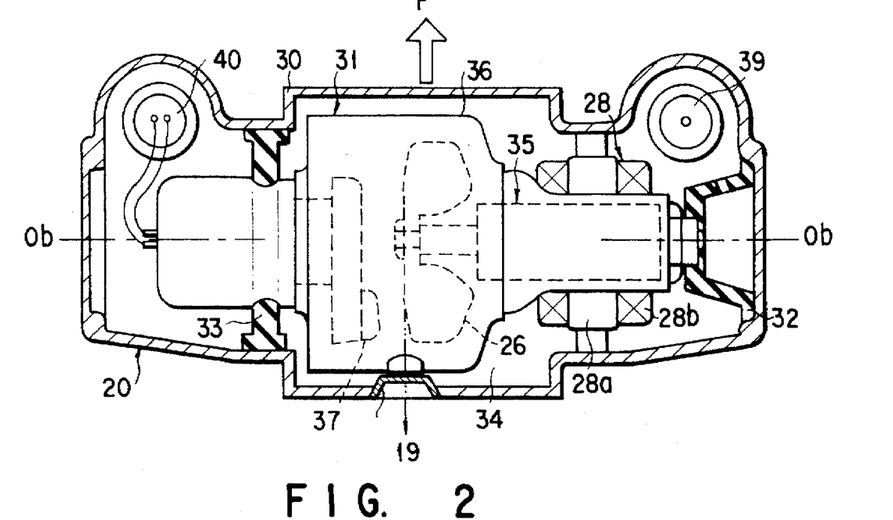
FIG. 2 is a schematic longitudinal sectional view of an X-ray tube device shown in FIG. 1.

As shown in FIG. 2, the X-ray tube device 20 incorporates an X-ray tube 31 of a rotary anode type fixed by insulating supports 32 and 33 in an X-ray tube accommodation vessel 30. An insulating oil 34 is filled in the internal space of the X-ray tube device 20. The X-ray tube device 20 also comprises a stator 28 for rotating a rotary structure 35 and the anode target 26 in the X-ray tube. Reference numeral 36 in FIG. 2 denotes a vacuum vessel of the X-ray tube; 37, a cathode; 38, an X-ray radiation gate; 39, an anode cable connector; and 40, a cathode cable connector. During rotation of the gantry rotary section of the CT scanner shown in FIG. 1 in the direction indicated by the arrow 18, i.e., in the helical scan mode, an outward centrifugal force in the upper direction (FIG. 2) indicated by an arrow F acts on the X-ray tube device 20.

In the vacuum vessel 36 for the X-ray tube 31 of the rotary anode type whose main part is shown in FIGS. 3 to 5A and 5B, the disk-like anode target 26 consisting of a heavy metal is integrally fixed to a rotating shaft 41 projecting from one end of the cylindrical rotary structure 35. The cathode 37 for emitting an electron beam is disposed to oppose the focal plane of the anode target 26.

A columnar stationary structure 42 is coaxially fitted in the cylindrical rotary structure 35, and a thrust ring 43 is fixed to the opening of the rotary structure. The end portion of the stationary structure 42 serves as an anode terminal 42a, and part of the anode terminal 42a is hermetically joined to a glass cylindrical vessel portion 36a of the vacuum vessel. A pair of radial hydrodynamic bearings 44 and 45 and a pair of thrust hydrodynamic bearings 46 and 47 as shown in the prior-art publication described above are formed at the fitting portion of the rotary structure 35 and the stationary structure 42.

Figure 4:
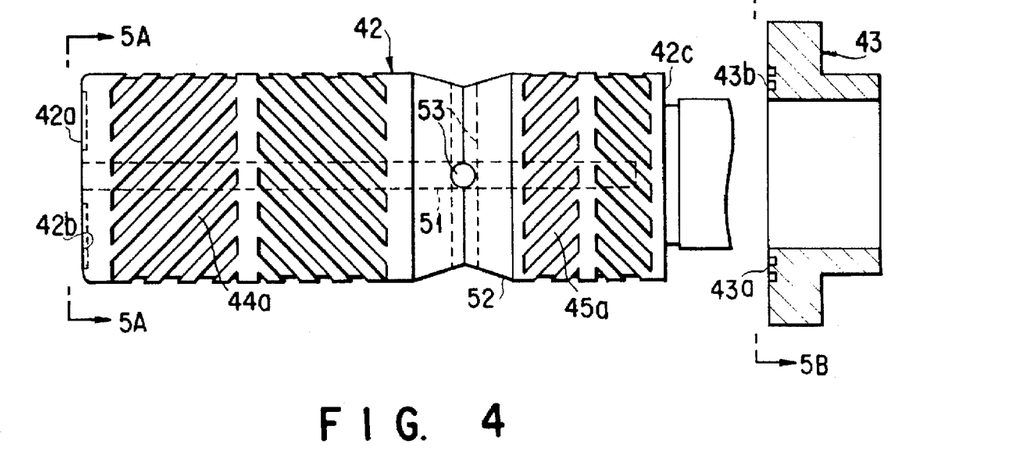
FIG. 4 is a plan view showing part of the X-ray tube shown in FIG. 3.
Figure 5A:
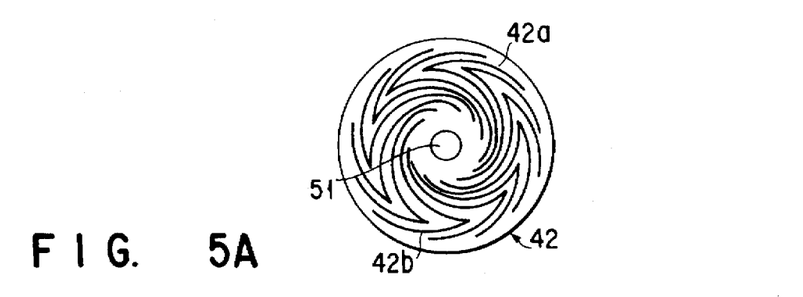
FIGS. 5A and 5B are plan views each showing part of the X-ray tube shown in FIG. 3.
Figure 5B:
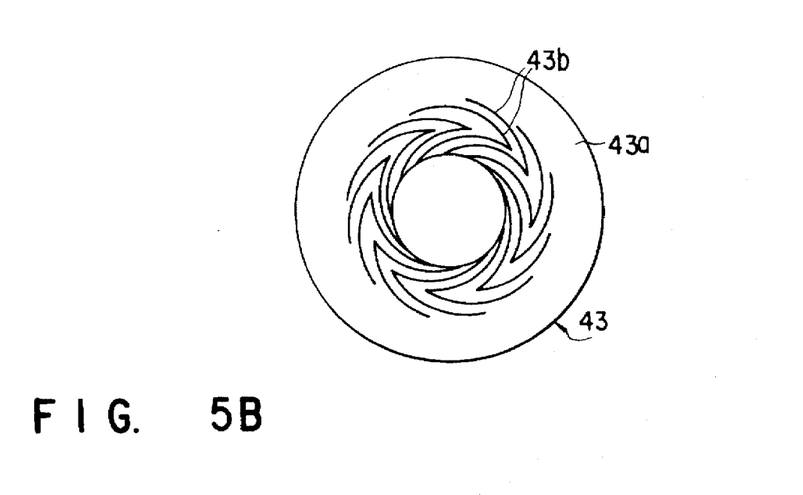

The radial hydrodynamic bearings 44 and 45, whose part is illustrated in FIG. 4, comprise a pair of helical grooves 44a and a pair of helical grooves 45a which are herringbone patterns formed on the outer bearing surface of the stationary structure 42, and inner bearing surfaces of the rotary structure 35. One thrust hydrodynamic bearing 46 comprises a helical groove 42b as a circular herringbone pattern (FIG. 5A) formed on a distal end shaft reception surface 42a of the stationary structure 42, and the bottom surface of the rotary structure. Note that FIG. 5A is a plan view taken along the line 5a—5a of FIG. 4. The other thrust hydrodynamic bearing 47 comprises a helical groove 43b as a circular herringbone pattern (FIG. 5B) formed on a bearing surface 43a of the thrust ring 43 serving as part of the rotary structure 35, and a bearing surface 42c of the shoulder portion of the stationary structure. Note that FIG. 5B is a plan view taken along the line 5b—5b of FIG. 4. The helical groove formed in the bearing surface constituting each bearing has a depth of about 20 µm.

During the operation, the bearing surfaces of the bearings of the rotary and stationary structures keep a bearing gap of about 20 µm. A lubricant storage chamber 51 consisting of a hole formed by boring the central portion of the stationary structure 42 in the axial direction is formed in the stationary structure 42 located on the central axis Ob of rotation. A small-diameter portion 52 is formed by slightly tapering the outer wall of the intermediate portion of the stationary structure 51, and a portion of the lubricant is stored in a cylindrical space defined by the small-diameter portion 52. Four radial paths 53 for communicating the lubricant storage chamber 51 at the central portion with the space defined by the small-diameter portion 52 are formed symmetrically at equal angular intervals. A liquid metal lubricant consisting of a Ga-In-Sn alloy is supplied to an internal space including the gap between the rotary and stationary structures, the helical groove of each bearing, the lubricant storage chamber 51, the space defined by the small-diameter portion 52, and the radial paths 53. The total volume of this metal lubricant is 60% of the total volume of the internal space.

The main part of the rotary structure 35 comprises a triple cylinder consisting of an inner bearing cylinder made of an iron alloy, an intermediate ferromagnetic cylinder made of iron, and an outer copper cylinder, which are integrally coupled to each other. These cylinders serves as the rotor of an electromagnetic induction motor together with the stator 28 disposed on the outer surface of the glass cylindrical vessel portion 36a which surrounds the rotary structure 35. The stator 28 comprises a cylindrical iron core 28a and a stator coil 28b wound on the iron core 28a. The stator 28 operates together with the ferromagnetic cylinder to generate a magnetic field for rotating the ferromagnetic cylinder. The rotation drive power is supplied from the stator drive power supply device 25 to this stator coil 28b to generate a rotation torque in the rotary structure in the X-ray tube.

Figure 3:
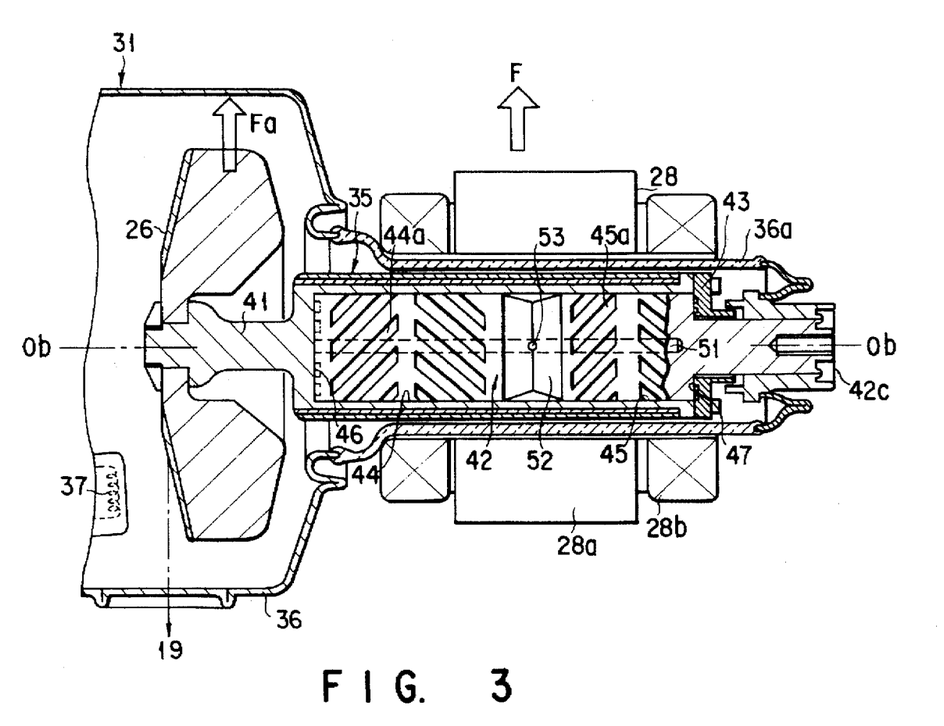
FIG. 3 is an enlarged longitudinal sectional view showing part of the X-ray tube shown in FIG. 2.

When the gantry rotary section 15 is rotated in the operation of the CT scanner, the upward centrifugal force as indicated by the arrow F in FIGS. 2 and 3 acts on the X-ray tube 31 of the rotary anode type, as previously described. The vacuum vessel 36 and the stationary structure 42 are mechanically fixed to the X-ray tube accommodation vessel, while the rotary structure 35 and the anode target 26 are rotated in a substantially floating state through the bearing gap with respect to the stationary structure 42. For this reason, the rotary structure 35 and the anode target 26 receive an upward (FIGS. 2 and 3) centrifugal force to be urged against the stationary structure 42. In particular, the bearing gaps of the radial hydrodynamic bearings 44 and 45 are wide became narrow in the lower positions in FIGS. 2 and 3 and wide in the upper positions in FIGS. 2 and 3. That is, the bearing gaps are nonuniform in the circumferential direction. In addition, the liquid metal lubricant is also pressed upward in FIGS. 2 and 3. When the anode target 26 is considerably heavier than the rotary structure 35 and the center of gravity is located on the anode target side, a centrifugal force Fa acting on the anode target portion is much larger than that acting on the rotary structure portion, thus further generating a force on the hydrodynamic bearings in a nonuniform torsional direction.

As can be apparent from the above description, during rotation of the gantry rotary section, the hydrodynamic bearings of the X-ray tube receive a high rotation resistance, i.e., a large rotation braking load. Therefore, the prescribed bearing performance obtained when the gantry rotary section is kept stopped cannot be maintained, and the rotation rate is greatly reduced.

Figures 6A, 6B:
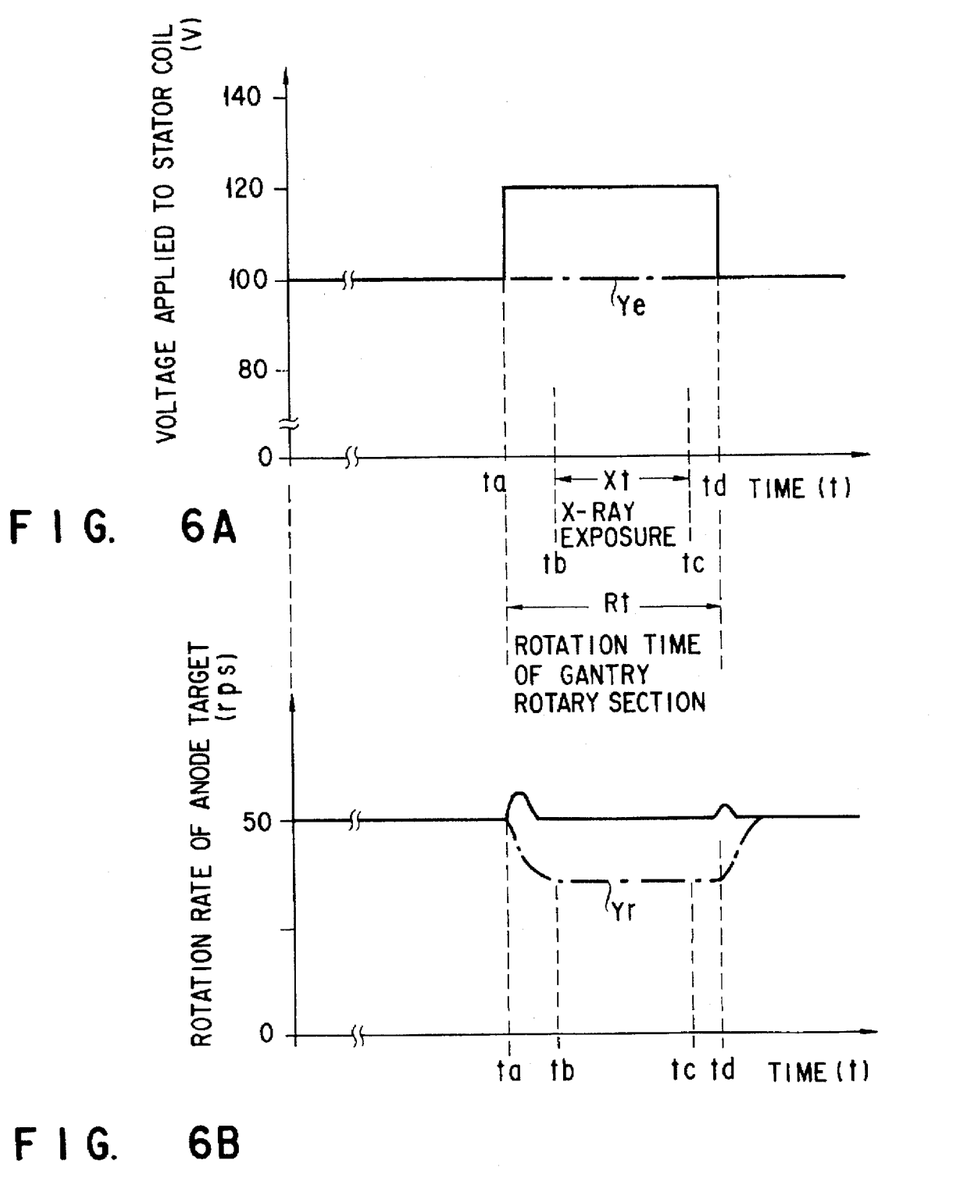
FIGS. 6A and 6B are sequence control charts for explaining the operation of the X-ray tube device shown in FIG. 1.

In the CT scanner of this embodiment, rotation drive control is performed, as shown in FIGS. 6A and 6B. More specifically, FIG. 6A shows the time control profile of a rotation drive voltage supplied from the rotation drive power supply device 25 to the stator coil 28 of the X-ray tube device, and FIG. 6B shows a change over time in the rotation rate of the anode target in accordance with this profile.

For one-day use of the CT scanner, the respective power supplies such as a main power/controller 29, the x-ray tube operation power supply device 24, and the rotation drive power supply device 25 are turned on. A rotation drive voltage of, e.g., 100 V is always applied to the stator coil of the X-ray tube device even in a non-photographic mode so as to be ready for a photographic mode for X-ray tomography, thereby generating a rotation torque in the rotary structure 35. The rotary structure 35 and the anode target 26 of the X-ray tube are continuously rotated at about 50 rps. Starting for photographic operations of the X-ray tomographic apparatus in a given unit is not limited to starting for one day, but may be starting for half a day during which photographic operations are scheduled, starting for two days, starting for a week, or the like. When the main power switch of the apparatus is turned on to start the apparatus, the rotary structure 36 of the X-ray tube is continuously rotated by continuously or intermittently supplying the rotation drive power at the end of photographic operations, i.e., when or just before the main power switch is turned off.

When X-ray tomography, i.e., a photographic mode is started, a control signal for the start of rotation of the gantry rotary section is generated from the main power/controller 29 at time ta. When rotation of the gantry rotary section 15 is started, the rotation drive voltage applied from the rotation drive power supply device 25 to the stator coil 28 of the X-ray tube device is simultaneously and automatically switched to, e.g., 120 V to increase the rotation torque for rotating the rotary structure 35 and the anode target 26 of the X-ray tube. Note that the rotation time of the gantry rotary section 15 is represented by a period Rt.

As described above, upon starting the rotation of the gantry rotary section 15, the rotation drive voltage to the stator coil 28 is simultaneously and automatically increased to 120 V. This voltage is kept supplied to the end of rotation of the gantry rotary section. If the rotation drive voltage (Ye indicated by a chain line) to the stator coil 28 is kept at 100 V which is the voltage prior to rotation of the gantry rotary section, the rotation rate of the anode target 26 falls to about 35 rps indicated by a chain line Yr in FIG. 6B due to the influence of the centrifugal force generated upon rotation of the gantry rotary section 15. In this embodiment, however, the rotation rate of the anode target is kept at about 50 rps, as indicated by the solid line. The rotation drive force is increased when the rotation load of the rotary structure of the X-ray tube is increased by the centrifugal force upon rotation of the gantry rotary section, and a necessary and sufficient dynamic pressure can be generated by the bearing section, thereby increasing the rotation rate. Therefore, radiation from the X-ray tube can be controlled at a necessary and sufficient X-ray dose in the X-ray photography. Note that the rotation drive voltage (Ye) of 100 V is a value at which the rotation rate of the anode target 26 is kept at about 50 rps required for X-ray radiation while the gantry rotary section 15 is at rest.

In the photographic mode, a control signal for starting X-ray radiation from the X-ray tube is supplied from the main power/controller to the X-ray tube operation power supply device at an arbitrary timing when the gantry rotary section 15 is kept rotated. A high voltage is applied to the X-ray tube to radiate X-rays from the X-ray tube for a predetermined period of time, thereby performing X-ray photography. This X-ray exposure time (Xt) is the time interval from time tb to time tc. For example, the X-ray exposure time is about one minute in helical scan. At time td upon completion of X-ray exposure, rotation of the gantry rotary section is stopped, and at the same time, the rotation drive voltage to the stator coil is automatically returned to the original voltage of 100 V. The anode target of the X-ray tube is kept rotated at about 50 rps and ready for the next X-ray photography.

Figure 7:
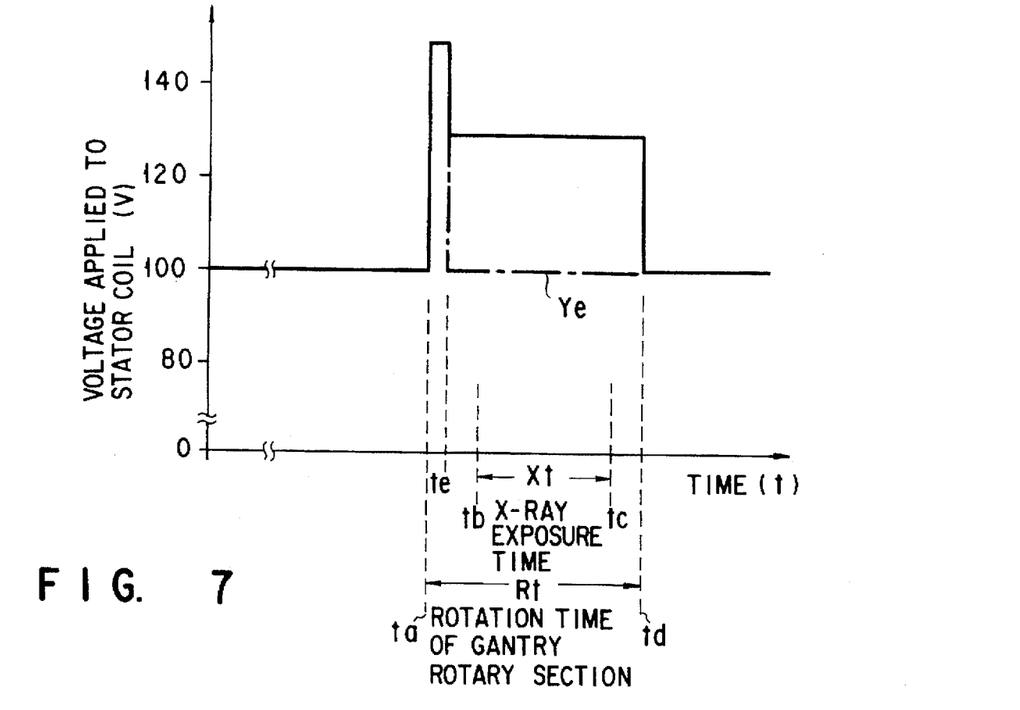
FIG. 7 is a sequence control chart for explaining the operation of an apparatus according to another embodiment of the present invention.

In another embodiment of FIG. 7, when rotation of the gantry rotary section is started at standby start time ta for performing X-ray tomography, a rotation drive power supply device 25 automatically switches the rotation drive voltage to the stator coil of the X-ray tube device to, e.g., 150 V. This rotation drive voltage is kept applied to a stator coil 28 for about three seconds (up to time te), thereby rapidly increasing the rotation rate of an anode target 26. Subsequently, the rotation drive voltage is automatically switched to 130 V, so that the rotation rate of the anode target is controlled to stay at about 80 rps. X-ray exposure (X) is then performed. After the gantry rotary section is stopped, the rotation drive voltage is automatically returned to the original voltage of 100 V, so that the anode target is kept rotated at 50 rps.

According to this embodiment, a decrease component caused by the centrifugal force is compensated by changing the rotation time (Rt) of the gantry rotary section and the rotation rate of the anode target for X-ray exposure time (Xt). In addition, the rotation rate of the anode target is further increased to increase the amount of electron beam incident on the target.

Figure 8:
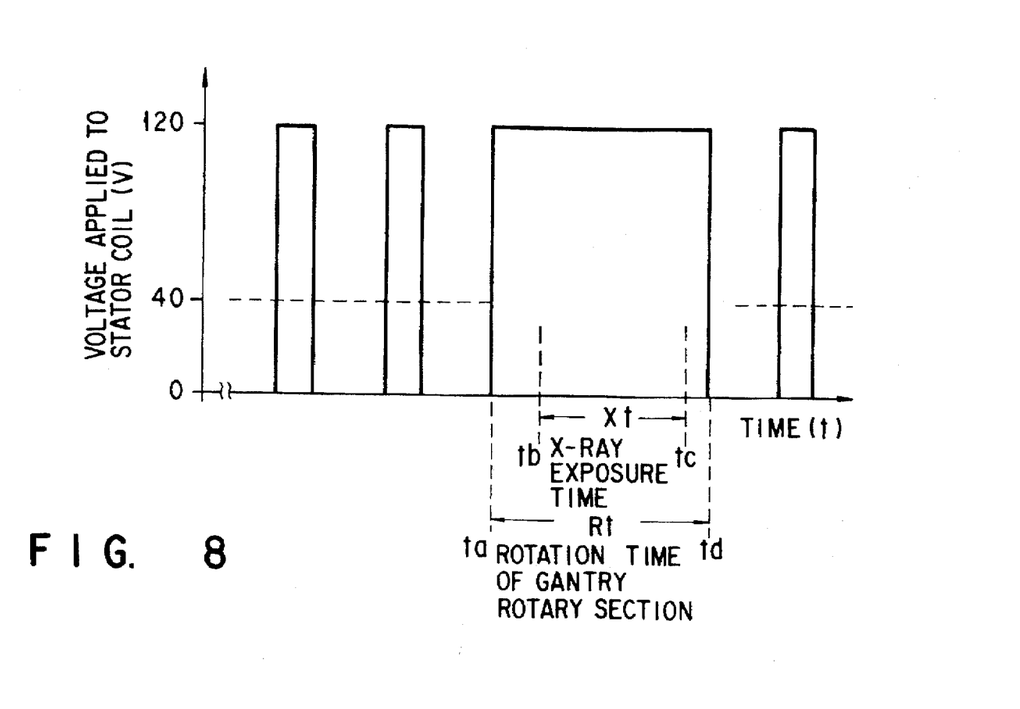
FIG. 8 is a sequence control chart for explaining the operation of an apparatus according to still another embodiment of the present invention.

In still another embodiment shown in FIG. 8, the standby time for X-ray photography is controlled. More specifically, a rotation drive power supply device 25 employs a control scheme for intermittently supplying a rotation drive voltage to a stator coil to save the rotation drive power. For example, a rotation drive voltage of 120 V is applied to a stator coil 28 for about one minute every three minutes. The average supply power corresponds to about ⅓ the continuous supply power, as illustrated by a dotted line.

In the photographic mode for X-ray photography, as in the previous embodiments, upon rotation of a gantry rotary section 15, the rotation drive voltage to the stator coil 28 is simultaneously switched to 120 V, and this voltage is continuously applied to the stator coil 28. Upon completion of rotation of the gantry rotary section, the rotation drive voltage to the stator coil 28 is returned to an intermittent application of voltage.

As described above, rotation torque control is performed such that the rotation torque of a rotary structure of an X-ray tube which is obtained during rotation of the gantry rotary section 15 in the photographic mode is switched to an average rotation torque larger than an average continuous rotation torque in the non-photographic mode prior to rotation of the gantry rotary section 15. Note that the average rotation torque is an average value of the rotation torques before and after rotation of the gantry in a unit time, e.g., in units of 5, 10, or 30 minutes.

Figure 9:
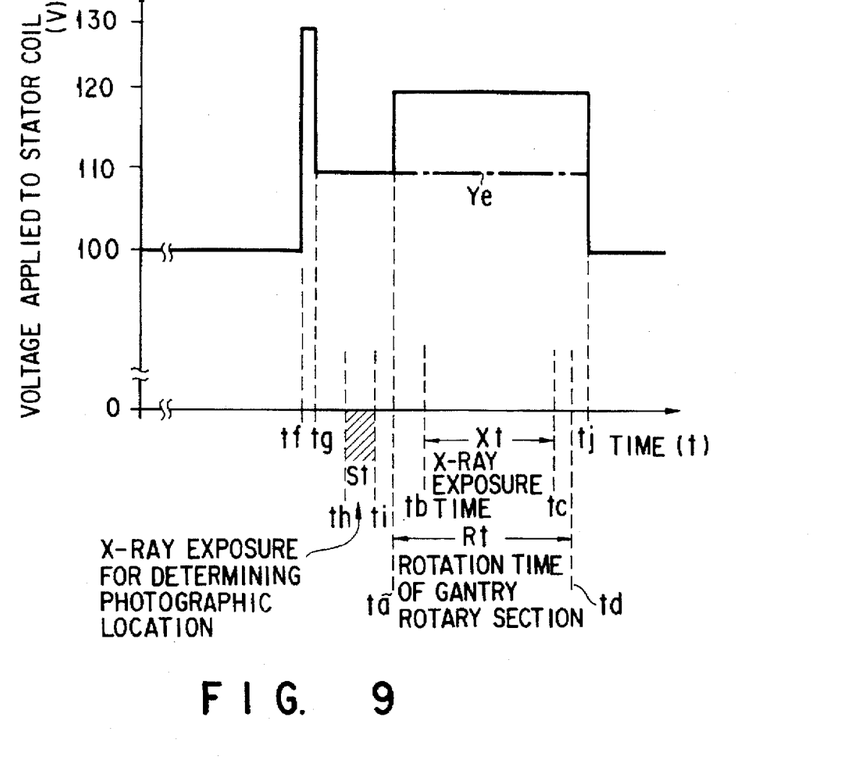
FIG. 9 is a sequence control chart for explaining the operation of an apparatus according to still another embodiment of the present invention.

Still another embodiment shown in FIG. 9 exemplifies a case wherein a mode for performing fluoroscopy to determine the photographic location for a tomographic image of an object to be photographed, i.e., a preliminary photographic mode is performed. More specifically, the rotation drive voltage applied to a stator coil 28 is switched from the continuous voltage of 100 V to 130 V. The voltage of 130 V is kept applied for three seconds to rapidly increase the rotation rate of an anode target 26. At time tg, the rotation drive voltage to the stator coil 28 is switched to 110 V to maintain the rotation rate of the anode target 26 at, e.g., 60 rps. During the time interval from arbitrary time th to time ti when the rotation rate is kept at 60 rps, X-ray exposure (St) is performed for fluoroscopy to determine the photographic location of the object to be photographed. At time ta after the photographic location is determined, rotation of the gantry rotary section is started, and at the same time the rotation drive voltage to the stator coil is switched to 120 V to increase the rotation rate of the anode target to, e.g., 80 rps. This rotation rate is then maintained. The above rotation drive voltage is a voltage for canceling the influence of the centrifugal force caused by rotation of the gantry rotary section and setting a higher rotation rate, i.e., the rotation rate of 80 rps. X-ray exposure (Xt) is then performed for tomography. After rotation of the gantry rotary section is stopped, the rotation drive voltage to the stator coil is switched to the original voltage of 100 V and ready for the next photographic operation.

Figure 10A:
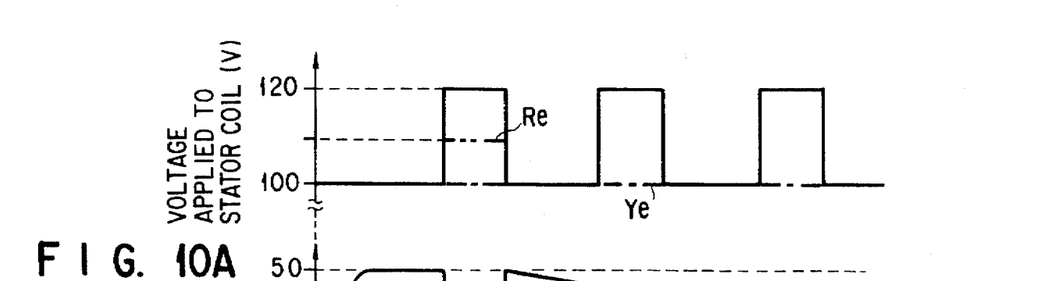
FIGS. 10A and 10B are sequence control charts for explaining the operation of an apparatus according to still another embodiment of the present invention.
Figure 10B:
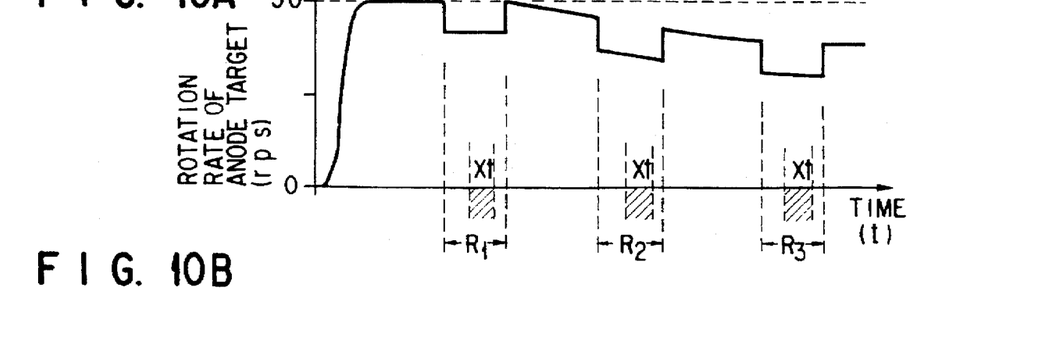

Still another embodiment shown in FIGS. 10A and 10B exemplifies an X-ray tomographic apparatus in which a decrease in rotation rate of an anode target caused by an increase in temperature of a stator is compensated when X-ray exposure is repeated. That is, the tomographic apparatus is started for one-day X-ray photographic operations, and a rotation drive voltage of 100 V is applied to a stator coil to rotate an anode target at a rotation rate of 50 rps.

The gantry rotary section is rotated for the first X-ray photography upon starting the tomographic apparatus to set the anode target to a predetermined rotation rate, and X-ray exposure (Xt) is performed in a rotation period of gantry R1 in FIGS. 10A and 10B. The anode target is gradually heated to increase the temperature of the stator coil of the stator together with the temperature of the hydrodynamic bearing section due to radiation heat and conduction heat. The winding resistance of the stator coil increases due to its power consumption and heat transferred from the anode target. By these causes, even if the rotation drive voltage applied to the stator coil is kept unchanged, the rotation rate of the anode target is gradually reduced. When X-ray photography is repeatedly performed for time intervals R2, R3, ..., as shown in FIG. 10B, the rotation rate of the anode target 26 is gradually lowered further. The rotation rate reduction curve in FIG. 10B is exaggerated to facilitate understanding. The rotation drive voltage for compensating for a decrease in rotation rate of the anode target which is caused by the centrifugal force upon rotation of the gantry rotary section and maintaining the original rotation rate of 50 rps which allows X-ray exposure even during rotation of the gantry is 108 V as indicated by reference symbol Re in FIG. 10A.

In this embodiment, during rotation of the gantry rotary section, the rotation drive voltage applied to the stator coil 28 is switched to a higher voltage (e.g., 120 V) than the above voltage of 108 V. More specifically, at or prior to the first X-ray exposure time in the initial state upon starting the tomographic apparatus, i.e., prior to an increase in temperature of the stator coil due to heat transfer from the anode target, control is performed to supply to the stator coil a voltage (i.e., a drive voltage exceeding 108 V in the above case) obtained by adding a higher drive voltage component than a drive voltage component (8 V in the above case) required for compensating for the decrease in rotation rate of the anode target which is caused by the centrifugal force upon rotation of the gantry rotary section 15. Note that this additional voltage component is preferably set to 1.2 times or more the minimum voltage component (8 V in the above case) for compensating for the decrease in rotation rate of the anode target which is caused by the centrifugal force generated upon rotation of the gantry rotary section. The adverse influence caused by an increase in temperature of the stator coil can be sufficiently eliminated in practical use even if X-ray exposure is repeated for a long period of time.

As described above, the rotation drive voltage applied to the stator coil in X-ray photography while rotating the gantry rotary section at a predetermined rotation rate is set to a voltage obtained such that a higher voltage component than the minimum voltage component required for compensating the decrease in rotation rate of the anode target which is caused by the centrifugal force generated upon rotation of the gantry rotary section and setting the above predetermined rotation rate is added to the rotation drive voltage for obtaining the same rotation rate as the predetermined rotation rate upon stopping rotating the gantry rotary section in the first X-ray exposure or prior thereto after the tomographic apparatus is started.

According to this embodiment, the rotation rate of the anode target during rotation of the gantry rotary section can be maintained at a sufficiently high rotation rate which can eliminate the adverse influence of the centrifugal force and the adverse influence of heat transfer from the anode target upon repeated X-ray exposure. For this reason, even if X-ray photography is repeated while rotating the anode target at a substantially constant rotation rate, the decrease in rotation performance of the stator which is caused by the increase in temperature of the target can be compensated, and a necessary and sufficient anode rotation rate can be maintained. Therefore, an X-ray tomographic apparatus having a higher reliability can be realized.

The present invention is also applicable to an apparatus in which the central axis of rotation of an X-ray tube of a rotary anode type is directed in the rotational direction of a gantry rotary section. In this case, loads generated upon rotation of the gantry rotary section act not only on the radial hydrodynamic bearings but also on the thrust hydrodynamic bearings. The present invention can prevent the decrease in rotation rate caused by the above loads.

It is preferable that the rotation rates of the anode target of the X-ray tube and the rotation rate of the rotary structure be controlled to fall within the range of 2,000 rpm to 6,000 rpm. Therefore, a necessary and sufficient X-ray dose can be obtained without undesirably increasing the rotation drive power supplied to the stator coil.

There may be provided a control means for changing the rotation rate of the gantry rotary section and increasing/decreasing the rotation torque for rotating the rotary structure and the anode target upon supplying the rotation drive power to the stator coil so as to correspond to the rotation rate of the gantry rotary section.

The rotation torque changing control means for rotating the rotary structure and the anode target of the X-ray tube may use at least one of a power, voltage, and current supplied to the stator coil, or a frequency thereof.

As has been described above, according to the present invention, an undesirable decrease in rotation rate of the anode target of the X-ray tube in X-ray tomography upon rotation of the gantry rotary section can be eliminated, and an excellent X-ray tomographic image can be obtained upon radiation at a necessary and sufficient X-ray dose. Therefore, X-ray tomography with a high reliability can be assured.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalent.

We claim:

1. A X-ray tomographic apparatus for photographing an X-ray slice of an object to be photographed, comprising:

an X-ray tube having an anode target, a cathode for emitting an electron beam toward said anode target, a rotary structure to which said anode target is fixed, a stationary structure coaxially fitted in said rotary structure, and a hydrodynamic bearing provided with between said rotary and stationary structures, in which a liquid metal lubricant having a predetermined melting point is filled in a fitting portion;

means for energizing said X-ray tube to generate an X-ray;

a stator coil provided around said rotary structure of said X-ray tube to generate a magnetic field for rotating said rotary structure;

power supply means for supplying a rotation drive power to said stator coil to rotate said rotary structure;

detection means for detecting an X-ray emitted from said X-ray tube and passing through a region where the object to be photographed is placed;

holding means, having a frame assembly for maintaining said X-ray tube, and said stator coil in a predetermined layout, for holding said X-ray tube and said stator coil to be rotatable around the region where the object to be photographed is placed, while maintaining the predetermined layout;

rotation means for rotating said frame assembly; and control means for controlling to supply the rotation drive power to said stator coil, said control means supplying the rotation drive power to said stator coil prior to rotation of said frame assembly to continue rotating said rotary structure with a first average rotation torque, and rotating said rotary structure with a second average rotation torque larger than the first average rotation torque during rotation of said frame assembly.

2. An apparatus according to claim 1, wherein said anode target of said X-ray tube and said frame assembly have first and second central axes of rotation, respectively, and said anode target and said frame assembly are located such that the first and second central axes of rotation are substantially parallel to each other.

3. An apparatus according to claim 1, wherein said control means increases the rotation torque of said rotary structure of said X-ray tube prior to rotation of said frame assembly.

4. An apparatus according to claim 1, wherein said control means increases the rotation torque of said rotary structure of said frame tube simultaneously when or after rotation of said frame assembly is started.

5. An apparatus according to claim 1, wherein said control means maintains the rotary structure at a first rotation rate when the first torque is applied and at a second rotation rate when the second torque is applied, the first rotation rate being not less than 90% the second rotation rate.

6. An apparatus according to claim 5, wherein said control means maintains the second rotation rate within a range of 2,000 rpm to 6,000 rpm.

7. An apparatus according to claim 1, wherein said control means controls at least one of a supply power, a supply voltage, a supply current, and a supply frequency to said stator coil.

8. An apparatus according to claim 1, further comprising:

second control means for changing the rotation rate of said frame assembly, wherein said first control means changes the rotation torque in accordance with the rotation rate of said frame assembly.

9. An apparatus according to claim 1, further comprising:

a main power supply for energizing said X-ray tomographic apparatus, and wherein after said X-ray tomographic apparatus is started upon turning on said main power supply, said first power supply means always maintains rotation of said rotary structure when or immediately before said main power supply is turned off.

10. An X-ray tomographic apparatus comprising:

an X-ray tube having an anode target, a cathode for emitting an electron beam toward said anode target, a rotary structure to which said anode target is fixed, a stationary structure coaxially fitted in said rotary structure, and a hydrodynamic bearing provided between said rotary and stationary structures, in which a liquid metal lubricant having a predetermined melting point is filled;

a stator coil provided around said rotary structure of said X-ray tube;

a stator drive power supply device so connected as to supply a rotation drive power to said stator coil;

an X-ray detector for detecting an X-ray emitted from said X-ray tube and passing through a region where an object to be photographed is placed;

a gantry rotary section to which said X-ray tube and said stator coil are attached at predetermined positions, said gantry rotary section being disposed to rotate around the region where the object to be photographed is placed in X-ray photography; and control means for continuing rotation of said rotary structure of said X-ray tube with a rotation torque generated by a rotation drive power supplied to said stator coil prior to rotation of said gantry rotary section, performing first X-ray photography by X-ray exposure prior to the rotation of said gantry rotary section, and then performing second X-ray photography by X-ray exposure after said gantry rotary section is rotated and the rotation torque of said rotary structure of said X-ray tube is changed.

11. An apparatus according to claim 10, wherein a rotation torque of said rotary structure of said X-ray tube during rotation of said gantry rotary section is changed to a larger value than that prior to the rotation of said gantry rotary section.

12. An apparatus for photographing an X-ray slice of an object to be photographed, comprising:

an X-ray tube having an anode target, a cathode for emitting an electron beam toward said anode target, a rotary structure to which said anode target is fixed, a stationary structure coaxially fitted in said rotary structure, and a hydrodynamic bearing provided between said rotary and stationary structures, in which a liquid metal lubricant having a predetermined melting point is filled;

energizing means for energizing said X-ray tube to generate an X-ray;

a stator coil provided around said rotary structure of said X-ray tube to generate a magnetic field for rotating said rotary structure;

power supply means for supplying a rotation drive power to said stator coil to rotate said rotary structure;

detection means for detecting an X-ray emitted from said X-ray tube and passing through a region where the object to be photographed is placed;

rotation holding means, having a frame assembly for maintaining said X-ray tube, and said stator coil in a predetermined layout, for holding said X-ray tube and said stator coil to be rotatable around the region where the object to be photographed is placed, while maintaining the predetermined layout;

rotation means for rotating said frame assembly; and control means for applying first and second rotation drive voltages to said stator coil to perform rotation control for rotating said rotary structure, said control means energizing said X-ray tube while rotating said frame assembly at a predetermined rotation rate to apply the second rotation drive voltage to said stator coil in a photographic mode, and the first rotation drive voltage to said stator coil in a non-photographic mode in which said frame assembly is kept stopped, and the first and second rotation drive voltages being so determined as to rate prevent the rotation rate of said rotary structure from being reduced by a centrifugal force generated upon rotation of said frame assembly.

13. An apparatus according to claim 12, wherein the second rotation drive voltage is substantially not less than 1.2 times the first rotation drive voltage.

* * * * *